US009763398B2

(12) United States Patent
Deane

(10) Patent No.: US 9,763,398 B2
(45) Date of Patent: Sep. 19, 2017

(54) APPARATUS, METHOD AND SYSTEM FOR ALGAE GROWTH

(76) Inventor: Arthur Arnott Deane, Calgary (CA)

(*) Notice: Subject to any disclaimer, the term of this patent is extended or adjusted under 35 U.S.C. 154(b) by 774 days.

(21) Appl. No.: 13/501,689

(22) PCT Filed: Oct. 27, 2010

(86) PCT No.: PCT/CA2010/001715
§ 371 (c)(1),
(2), (4) Date: Jun. 19, 2012

(87) PCT Pub. No.: WO2011/050472
PCT Pub. Date: May 5, 2011

(65) Prior Publication Data
US 2012/0252103 A1    Oct. 4, 2012

Related U.S. Application Data

(60) Provisional application No. 61/255,416, filed on Oct. 27, 2009.

(51) Int. Cl.
*A01G 33/00*    (2006.01)
*A01H 4/00*    (2006.01)
(Continued)

(52) U.S. Cl.
CPC ............ *A01G 33/00* (2013.01); *A01H 4/001* (2013.01); *C12M 21/02* (2013.01); *C12M 23/22* (2013.01);
(Continued)

(58) Field of Classification Search
CPC ........ A01G 33/00; A01H 4/001; C12M 21/02; C12M 23/22; C12M 23/34; C12M 27/00; C12M 27/18; C12M 31/10; C12M 41/00
(Continued)

(56) References Cited

U.S. PATENT DOCUMENTS 3,172,235 A * 3/1965 Bjorklund ................. 435/286.5
3,986,297 A * 10/1976 Ichimura et al. .......... 435/292.1
(Continued)

FOREIGN PATENT DOCUMENTS

CA    2394518 A1    1/2003
SU    959697 A * 10/1982

OTHER PUBLICATIONS

Amanov et al, Derwent abstract of (SU 959697), Oct. 28, 1982.*
(Continued)

*Primary Examiner* — Gautam Prakash
(74) *Attorney, Agent, or Firm* — Bennett Jones LLP

(57) ABSTRACT

The cultivation, by optimized growth and harvesting of algae derived bio-mass may provide useful feedstock for various products and processes. The present invention provides an apparatus that allows for the optimized growth and harvesting of algae within a photo-bioreactor. The photo-bioreactor may include a channel and a propulsion unit for circulating an algae mixture through a channel while exposing the algae mixture to light to support photosynthesis and growth of the algae. A method is also provided for the optimizing the growth and harvesting of algae utilizing a number of different input streams. Further, a system including a programmable control assembly is provided for the growth and harvesting of algae.

11 Claims, 11 Drawing Sheets

(51) Int. Cl.
*C12M 1/00* (2006.01)
*C12M 1/02* (2006.01)
*C12M 1/34* (2006.01)
*C12M 1/42* (2006.01)

(52) U.S. Cl.
CPC ............ *C12M 23/34* (2013.01); *C12M 27/00* (2013.01); *C12M 27/18* (2013.01); *C12M 31/10* (2013.01); *C12M 41/00* (2013.01)

(58) Field of Classification Search
USPC .............................. 47/1.4, 17; 435/29, 292.1
See application file for complete search history.

(56) References Cited

U.S. PATENT DOCUMENTS

| | | | | |
|---|---|---|---|---|
| 4,051,626 | A * | 10/1977 | Trumley et al. | 47/17 |
| 4,269,709 | A * | 5/1981 | Rongved | 210/195.3 |
| 4,320,594 | A * | 3/1982 | Raymond | 47/1.4 |
| 7,578,933 | B1 * | 8/2009 | Selman | 210/167.21 |
| 7,824,904 | B1 * | 11/2010 | Dimanshteyn | C12M 21/02 362/101 |
| 2002/0034817 | A1 | 3/2002 | Henry et al. | |
| 2002/0117503 | A1 * | 8/2002 | Lundquist | B62B 5/0083 220/495.1 |
| 2007/0048859 | A1 * | 3/2007 | Sears | 435/289.1 |
| 2008/0274494 | A1 * | 11/2008 | Kertz | 435/29 |
| 2009/0151240 | A1 | 6/2009 | Kayama et al. | |

OTHER PUBLICATIONS

Eriksen, N. et al. On-line estimation of O2 production, CO2 uptake, and growth kinetics of microalgal cultures in a gas-tight photobioreactor; Journal of Applied Phycology, Apr. 1, 2007; vol. 19(2), pp. 161-174, ISSN: 0921-8971.

* cited by examiner

APPARATUS, METHOD AND SYSTEM FOR ALGAE GROWTH

FIELD

The present invention relates to a system for growing algae and more particularly for controlling the growing environment and harvesting process for algae bio-mass.

BACKGROUND

Commercial farming, including the growing and harvesting of algae, is of interest because the produced algae can have a variety of uses. For example, algae can produce bio-mass feed stocks for the production of bio-fuels such as: bio-diesel, bio-kerosene, bio-ethanol and the like.

One common way of commercially growing algae is to use an open system where the algae grow process is open to the elements. These open pond systems can best be described as a number of plastic or clay lined shallow dugouts, occupying hundreds of hectares of land area. Race track systems are one type of known open pond system.

The open pond algae grow operations do not allow control over the temperature and lighting of the algae, but instead rely on outside conditions, causing the growth rates of the algae to vary and making open pond type systems undesirable for some climates, including colder climates. Additionally, these operations can be vulnerable to contamination from other micro-organisms or other types of algae because of the openness to the environment. A further shortcoming of these open pond grow operations is that the depth of the ponds is typically kept relatively shallow to allow for sufficient penetration of the natural light.

Other approaches to growing algae include a clear, hanging bag and the clear plastic tube technologies. However, there are many innate problems associated with these approaches, primarily relating to durability and maintenance issues. Algae residue can build up inside the bags and block out sunlight, reducing the bags photometric grow efficiency; as a result the bags have to be regularly changed. The same fouling problems may occur in the clear plastic tubes. Additionally, the clear plastic tubes may degrade over time and have a limited life expectancy when exposed continuously to sunlight. This makes it necessary to replace the tubes every four or five years.

Additionally, many of these systems require an extensive and permanent installation to be constructed to provide the necessary infrastructure to support growth and harvesting operations, which can increase the land usage requirements.

Alternatives to the current state of the art for growing and harvesting algae are of interest as they may provide novel apparatus, methods and systems for growing and harvesting algae.

SUMMARY

In accordance with one aspect of the present invention there is provided an apparatus for the growth and harvesting of algae as described herein. The apparatus may include a light source, a trough for housing an algae mixture, the trough including an inlet and an outlet, a partition within the trough, a propulsion member for circulating the algae mixture within the trough, around the partition, and past the light source; a water-gas mixer for producing growth media, the water-gas mixer located upstream from the trough, the water-gas mixer including an inlet and an outlet, the outlet being in fluid communication with a conduit through which the growth media is introduced through the inlet of the trough; a harvester to receive the algae mixture from the outlet of the trough, the harvester configured for separating algae from the growth media; and an enclosure enclosing at least the trough.

In accordance with another aspect of the present invention there is provided a method of algae growth and harvesting, including introducing water and carbon dioxide to a mixer unit to produce a growth solution; introducing the growth solution to a purifier for purification and a filter for filtration; introducing the growth solution, a nutrient source and algae seed to an enclosed photo-bioreactor; circulating the growth solution and algae seed through a photo-bioreactor while exposing the growth solution and algae seed to light to form grown algae; and harvesting the grown algae from the enclosed photo-bioreactor.

In accordance with another aspect of the present invention a system for growing and harvesting algae is provided. The system includes sources of water, nutrients, carbon dioxide and an algae seed source; a water-gas mixer to receive and mix the water and carbon dioxide to produce a growth medium stream; a purification unit to receive the growth medium stream and to purify the growth medium stream; a filtration unit to receive and filter the growth medium stream; an enclosed photo-bioreactor to receive the growth medium stream and the algae seed source for circulating a mixture of the growth medium stream and the algae seed source around a partition and a light source to form an algae growth; a harvesting unit to harvest the algae growth; and a programmable control assembly for controlling operations of the system.

It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects, all without departing from the spirit and scope of the present invention. Accordingly the drawings and detailed description are to be regarded as illustrative in nature and not as restrictive.

BRIEF DESCRIPTION OF THE DRAWINGS

Referring to the drawings wherein like reference numerals indicate similar parts throughout the several views, several aspects of the present invention are illustrated by way of example, and not by way of limitation, in detail in the figures, wherein.

DETAILED DESCRIPTION OF VARIOUS EMBODIMENTS

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

Apparatus

In an embodiment of the present invention, an apparatus for the growth and harvesting of algae is described herein. The apparatus may include at least one photo-bioreactor including a partition, an agitator, a propulsion member, and a light source. Further, the at least one photo-bioreactor may be within an enclosure allowing for greater control over the photo-bioreactor's environment. The photo-bioreactor may receive growth media that is produced within an upstream water-gas mixer. The growth media may further be purified and filtered prior to introduction into the photo-bioreactor. While in the photo-bioreactor, the growth media is mixed with algae seed, also termed inoculate, and propelled about a circuitous path, for example about the partition, while being exposed to the light source causing the growth of algae. Algae may then be routed from the photo-bioreactor into a harvester. Harvested algae may be of interest for various applications, as described herein further below.

Figure 1:
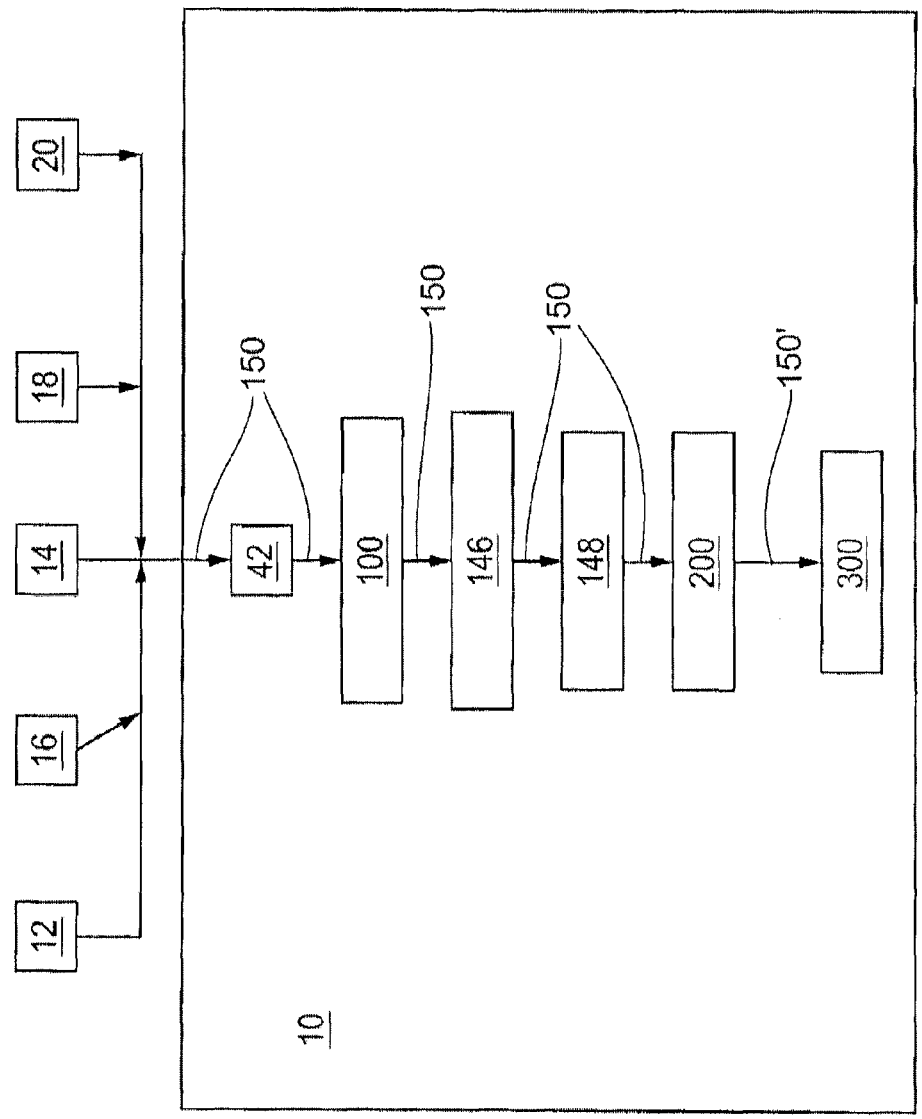
FIG. 1 is a block diagram of an algae growing and harvesting apparatus in accordance with an example embodiment of the present invention.

In reference to the Figures, FIG. 1 provides a block diagram illustration of an example embodiment of an apparatus 10 for growing and harvesting algae. The apparatus utilizes a number of different source inputs such as: a water source 12, carbon dioxide (CO2) source 14, a nutrient source 16, a heat source 18 and an electricity source 20. These inputs are utilized, as described herein further below, at various points within the apparatus to cultivate the growth and harvesting of algae in a controlled manner.

The water source may be any accessible source of water, including both fresh water and saline. As an example, water source 12 may be a municipal water source, a well, an aquifer, and any surface water such as an accessible river, stream, pond, lake or any oceanic body. One advantage of the present invention may be that the water source may further be a wastewater source. For example, wastewater from a wastewater-producing business, nearby municipal water treatment facility, etc. may be used in the algae growing apparatus 10.

The requirements for the growth of algae may vary among the species of algae being grown; however, the requirements are generally understood to include at least the following: water, carbon dioxide, phosphorous, nitrogen and light.

A source of CO2 14 may be any accessible source of carbon dioxide, for example flue gases from coal fired power plants, cement plants, petroleum refinery plants, fertilizer plants, bio-gas production facilities and any waste streams of CO2 that may be a by-product of many industrial applications.

Nutritional source 16 for the growth of algae may be provided by a variety of sources for example, an anaerobic digester 22 or by-products from bio-gas production, etc. For example, the anaerobic digester 22 can be used to convert organic waste from an agricultural source, such as grain production or a feed lot, into a bio-gas 24 and liquid fertilizer 26. Bio-gas 24 may include both methane and CO2; therefore, anaerobic digester 22 may provide another source of CO2 14. Liquid fertilizer 26 can contain nutrients, for example phosphorous and nitrogen, which may increase the growth of algae and can be used in the apparatus 10. Anaerobic digester 22 may also at least partially sterilize liquid fertilizer 26, for example by killing all germs, spores and other microbes that may contaminate the growth of algae.

In one aspect, nutritional source 16 may also be a commercially available fertilizer, for example, a soluble granular fertilizer. Commercially available fertilizer may be sterilized by, for example, exposure to ultraviolet light if necessary.

As will be explained further below, nutritional source 16, water 12 and CO2 14 may be mixed together to form a growth medium 150 for the growth of algae.

Source of electricity 20 may take various forms. As an example, bio-gas 24 produced by the anaerobic digester, including methane, may be used in a gas turbine generator 32 to provide electricity 20. However, electricity may also be sourced from utility grids, solar panels, wind turbines, geothermal sources and any other electricity streams, even some that may be considered a waste electricity stream from any source.

Source of heat 18 may be any accessible source of heat, for example a steam boiler 34 that may be powered by turbine generator 32. Heat may also be collected along the various input streams, e.g. waste heat from anaerobic digester 22, bio-gas 24, gas turbine 32, any source of flue gases 36, etc.

In an example embodiment, the heat may be directed to a heat exchanger 38 to control the temperature of the water source input, and as will be further described below, heat may be directed towards one or more heat units 40 associated with a photo-bioreactor 200.

As one may now further appreciate, the precise source of each of the aforementioned inputs is not essential to the functionality of the present invention. There are a number of approaches by which the ecological and land-use footprint of a given algae growth and harvesting apparatus may be efficiently managed. For example, any water source 12, CO2 source 14, nutrient source 16, heat source 18 and electricity source 20 that are accessible as an industrial waste stream may reduce or eliminate the necessity of sourcing from equipment ancillary to apparatus 10.

As another example, in one aspect, any flue gases or CO2 gases generated internally from the apparatus or externally, for example, from industrial plants, coal fired power plants, refineries, etc. can be continuously pressure-fed to the water gas mixing unit 100 through a pre-dissolving unit 42, such as a micro bubble pump, high shear static mixer, etc. to dissolve the gasses in the water prior to distributing the water gas mixture through the water gas mixing unit 100.

Water Gas Mixing Unit

The water gas mixing unit may permit the use of various of the aforementioned inputs to produce a growth 150 medium for the growth of algae. As will be disclosed further herein below, water-gas mixer unit 100 may also prestage the growth medium in order to manipulate the optimal conditions, including: temperature, pH, and nutrient levels, etc. of the growth medium.

Figure 5:
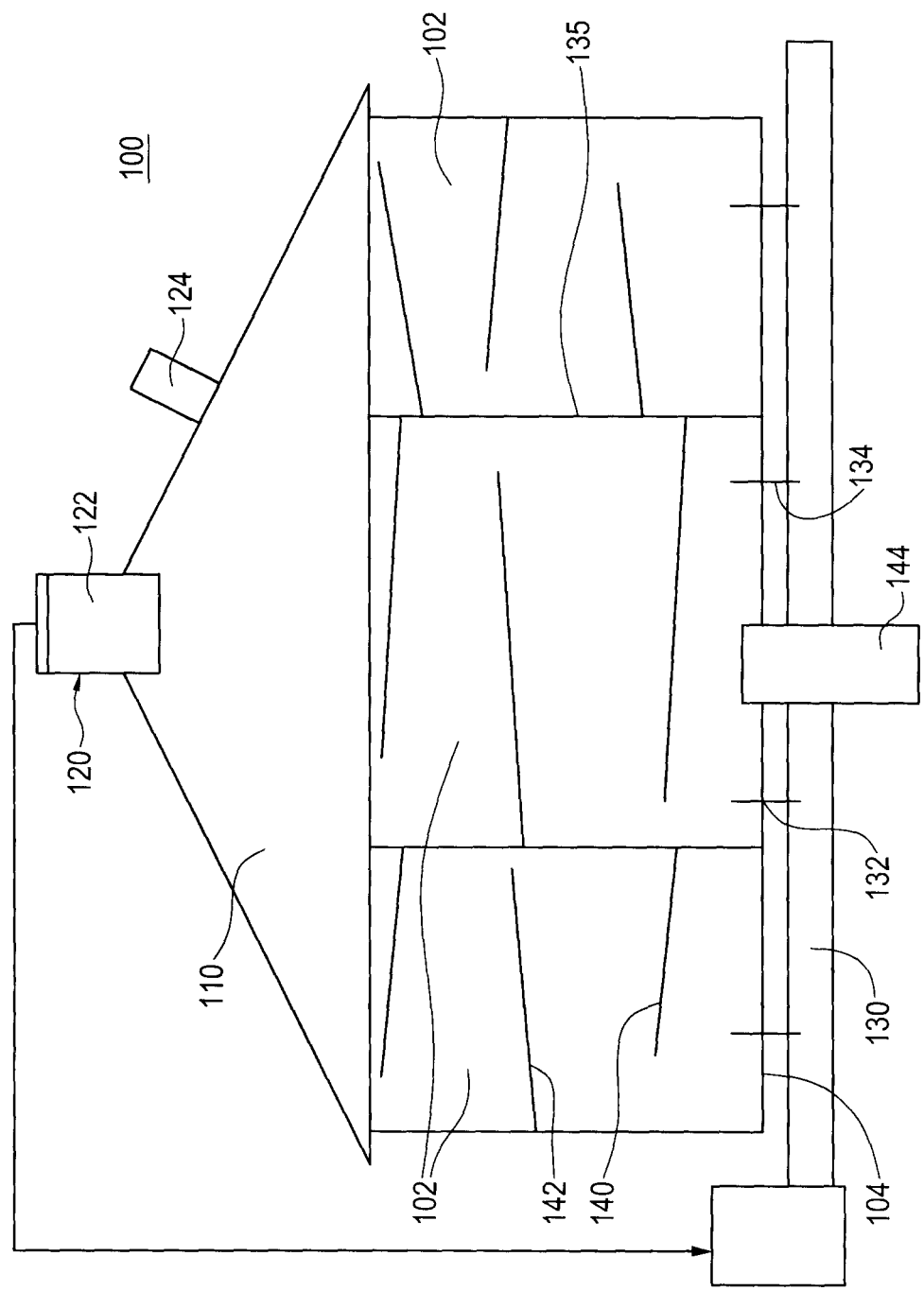
FIG. 5 is a cross-sectional, side view along the mid-line of an example embodiment of the water-gas mixer unit.

FIG. 5 illustrates an example embodiment of a water gas mixing unit 100, which can be formed from a number of square or rectangular tanks 102 connected inside a portable insulated steel skid 104. Each tank 102 can have a lid 110 that can be connected onto the top rim of the tank 102. The lid 110 can cover the tank 102 entirely and have an egress 120 that allows gases escaping from the water and accumulating at the top of the tank 102 to be re-circulated back through the water continuously. For example, egress 120 may house an air compressor or vacuum pump 122 to draw escaping gases out from the tank and re-circulate the escaped gases back to the pre-dissolving unit.

Lid 110 may also include a two-way pressure relief valve 124, such as a ball-valve, with a HEPA filter to relieve any problematic overpressure or pressure buildup or lock that may form within the tank.

As described above, skid 104 may be used to support the tanks 102. Skids can be an all-steel constructed module with dimensions 53' long by 14' wide by 12.5' high, constructed of 8" tubular HSS welded to form a typical skid sub-base with ¼" steel checker plate flooring. The side and end-wall framing may be 6" by 2.5" by 10' high tubular HSS spaced 8' apart, with lighter framing supports welded every 4' between each 10' upright. The exterior wall panels can include 3/16" molded steel sheeting and medium-gauge perforated interior wall sheeting with insulation between the outer and inner sheeting. The hollow interior of the HSS tubes of the walls and sub-flooring framing can be insulated as well. The inside of such a portable skid building may house two rectangular tanks 102, each measuring 20' long by 10' wide by 8' high plus a 1' high lid.

One or more pipes can feed water, flue gases and nutrients from pre-dissolving unit 42 into a manifold plenum distribution system 130. Manifold system 130 can run the entire length of the tank 102. The manifold system 130 can have a series of ports 132 and associated connections 134, for example piping, that provide fluid communication between the manifold system and the bottom of the tank 102. The manifold system 130 can be formed of tubing, piping, valves, etc. configured to maintain consistent pressure throughout the manifold system 130. Piping can tie the pre-dissolving unit and the manifold plenum distribution system 130 to the water gas mixing unit 100.

In an alternative embodiment, manifold system 130 may be comprised of a plurality of pipes, each with its own series of ports to provide fluid communication with the tank.

The tanks can be constructed with removable panels 135 which have a number of overlapping baffles 140 that may extend, substantially normal to removable panels 135. In one aspect, the lower surfaces 142 of the baffles can be abrasive to increase the friction and slow the passage of liquids and gases over the surface of the baffle 140, therefore increasing the travel residence time of the gas within the solution. The baffles 140 can create a tortuous path that the atomized gas bubbles must take in order to escape the water. The tortuous path may hold the gases in the water longer as the gases make their way to the top of the tank 102. As the gases run along the abrasive underside of the baffles 140, traversing from baffle 140 to baffle, the gases can be further scrubbed, dissolving much of the constituent elements into the water. The gas escaping the water may be collected in an air space in the top of the tank 102 and can re-circulated through the egress 120 in the lid 110, back to pre-dissolving unit 42 or to atmosphere.

As described above, increased scrubbing of $CO_2$ may enrich the water solution with $CO_2$. By using various techniques, such as temperature and pH control, the $CO_2$ levels of the growth medium may be regulated to ensure optimal levels. For example, lower temperatures may be used to increase $CO_2$ levels within the growth medium and pH may be retained between an approximate range of 6.0 and 8.5 with the use of a buffer for example, potassium hydroxide. As one may appreciate, various other techniques may be utilized to optimize the $CO_2$ levels within the growth medium.

Baffles 140 may extend from removable panel 135 at various angles. For example, the angle between lower surface 142 of baffles 140 and the removable panel may be either acute or obtuse depending upon whether the operator is inclined to increase or decrease the residence time of the gases within the solution. In reference to FIG. 5, obtuse angles between the lower surface of the baffles and the removable panels are shown.

In one embodiment, flue gases may contain other chemical constituents, for example nutrients like phosphates and nitrates. Flue gases may be dissolved into the water by the pre-dissolving unit and the nutrients may be scrubbed from the dissolved flue gas into the growth medium by way of baffles 140. As one can appreciate, specific downstream purification units 146 may be employed in such an embodiment, so that phosphates and nitrates are not removed from the growth media. One example of a specific purification unit may be an ultraviolet purification system.

Access ports (not shown), such as tap valves may be provided in one or more side walls of tank 102 so that samples of the grow media solution may be extracted from the tank for testing to facilitate optimization of the conditions, such as temperature, pH, $CO_2$ and nutrient levels etc. of the grow media. If the conditions of the growth media are outside optimal ranges, as determined by the algae species to be grown in a given batch of media, the operator may manipulate tank conditions, or the conditions upstream of the tank for example at the pre-dissolver unit or elsewhere. For example, the operator may re-circulate escaped gases to increase the concentration of nutrients, the operator may supplement the water source with different temperature water to optimize the temperature of the growth media, etc. As one can appreciate, a number of techniques may be employed by the operator to ensure that the growth media is within optimal conditions for the algae species to be grown.

Further, sight glass levels (not shown) may provide a window through which the volume levels of the liquids within tank 102 may be visually confirmed and evaluated.

In an alternative embodiment, tank 102 may include various sensors (not shown) for detecting pH, temperature, turbidity, nutrient levels, etc. The sensors may detect and provide signal information, either analogue, digital or the like to a central processor (not shown), for example a computer, which, through a pre-programmed software program and a feedback loop may optimize the growth media by increasing or decreasing the temperature, pH levels, nutrient levels and the like. In this manner, optimization of the growth media may be automated to prescribed, optimal conditions for a given target species of algae that is going to be seeded in each batch of growth media.

When the growth media has filled the tank and the operator, or an automated control system, has verified or optimized the conditions of a given batch of the growth media, one or more drains 144 in the floor of the tank may be opened, manually or by an automated process, to gravity drain the batch of growth media out of tank into a conveyance pipe to route the growth media to a purification unit 146 and a filter unit 148.

Referring again to FIGS. 1 and 2, after drainage from the water-gas mixer 100, growth medium 150 may then pass through purification unit 146 and filtration unit 148 to create a cleaned and filtered CO2 enriched growth medium 150 that is optimized for the growth of algae. Purification unit 146 may, for example, be an electrochemical purification unit or an ultraviolet emission purifier, as known in the art. Purification unit 146 may inactive contaminants, such as pathogens, and cause undesirable elements and impurities, except CO2 and other nutrients, to precipitate and possibly flocculate where they can be filtered by filtration unit 148 and removed from the growth media solution. Filtration unit 148 may, for example be a filter press that is selectable in terms of the size of impurities that are filtered from growth medium 150.

The purified and filtered growth medium can then be routed through an outlet pipe 152 or through a common manifold to an inlet pipe 154 which connects to one or more photo-bioreactors 200 to be used to grow algae. Excess wastewater may be routed to a water storage facility for storage and later use. Excess wastewater may also be directed back to the water gas mixing unit for re-use in producing growth medium 150.

In one embodiment, nutrition source 16 may be mixed with growth media solution 150 prior to routing to one or more photo-bioreactors 200. If nutrition source 16 contains impurities, it may be purified by any number of appropriate purification procedures, for example exposure to an ultraviolet emission purifier. Following purification, nutrition source 16 may be mixed with growth media solution 150 and then routed to the one or more photo-bioreactors 200.

In another embodiment, nutrition source 16 may be purified and mixed with water source 12 prior to routing to the gas-mixing unit 100 so that sterilized nutrition source 16, water source 12 and CO2 source 14 are all mixed and incorporated into growth media solution 150 in the pre-dissolving unit 42 or in the water gas mixing unit prior to routing to one or more photo-bioreactors 200. In this embodiment, the conditions of the growth media solution 150, including the nutrient source, may be purified, filtered and optimized prior to routing to the one or more photo-bioreactors.

Photo Bioreactor

The growth medium can be seeded with algae seed in the photo-bioreactors 200. After the growth medium is seeded, it is referred herein as an algae mixture 150'. Once the algae has grown to a desired density, the algae mixture can be removed from the photo-bioreactors 200 and routed to a strainer harvester so that the algae collected can be used as a biomass feedstock for bio-fuels, pharmaceuticals, nutraceuticals, etc.

As one can appreciate, the desired end-product for the algae-derived biomass feedstock may determine the species or strain of algae seed used. As will be appreciated from the description below, various embodiments of the photo-bioreactor may provide the advantage of producing larger volumes of algae in a smaller geographic area than some of the known algae growth and harvesting apparatuses. One aspect of the present invention may also provide for production of larger volumes of algae than the known hanging bag or clear tube systems.

The following non-exhaustive list provides some examples of the algae species of interest:

*Chlorella kessleri*; *Botryococcus braunii*; *Scenedesmus obliquus*; *Dunaliella tertiolecta*; *Neochloris oleoabundans*; *Scenedesmus dimorphus*; *Euglena gracilis*; *Phaeodactylum tricornutum*; *Pleurochrysis carterae*; *Prymnesium parvum*; *Tetraselmis chui*; *Tetraselmis suecica*; *Isochrysis galbana*; *Nannochloropsis salina* or *Nannochloris oculata*; *Nannochloris atomus Butcher*; *Nannochloris maculata Butcher*; *Nannochloropsis gaditana Lubian*; *Nannochloropsis oculata*; *Botryococcus brauml*; *Nannochloris* species; *Spirulina* species; *Chlorophyceae* species; and *Bacilliarophy* species.

Figure 8:
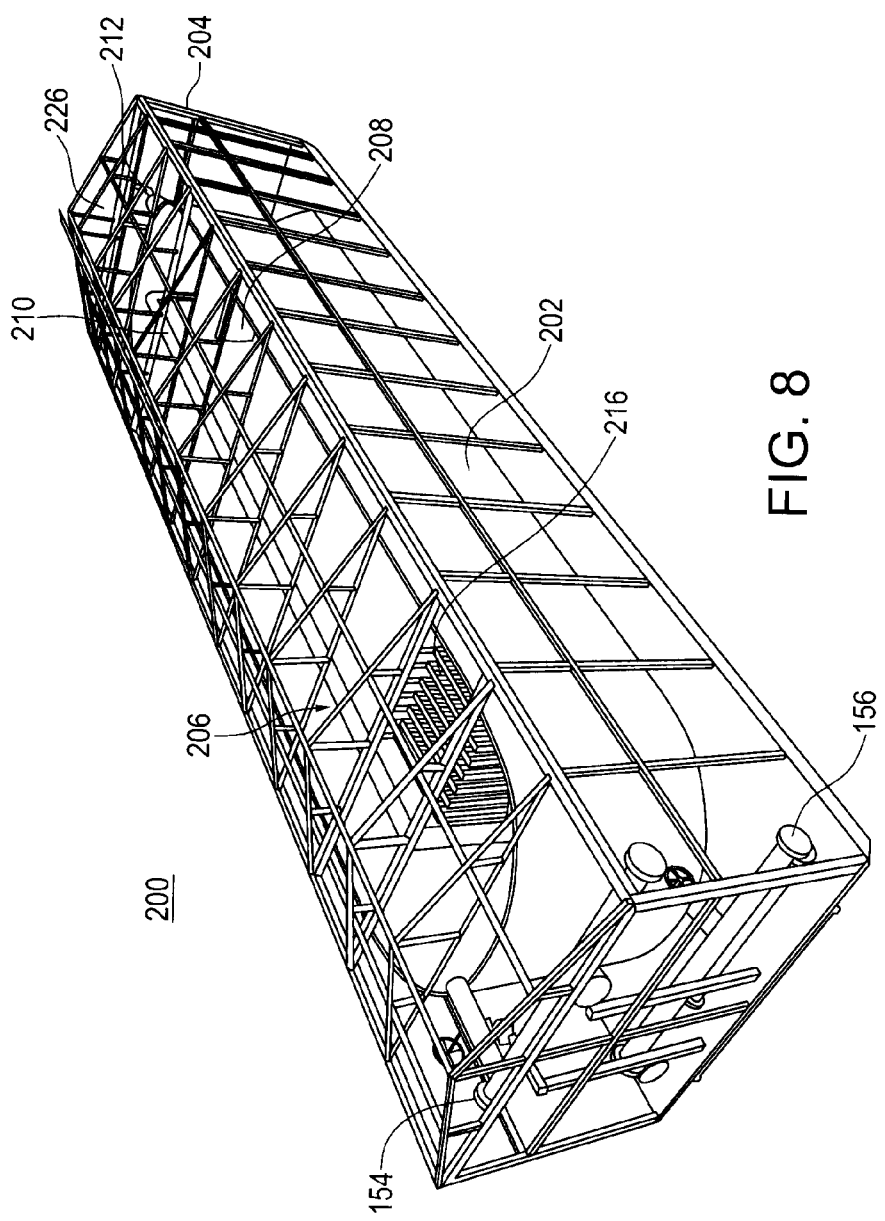
FIG. 8 is a perspective view of an example embodiment of a photo-bioreactor within an example embodiment of an enclosure.
Figure 9A:
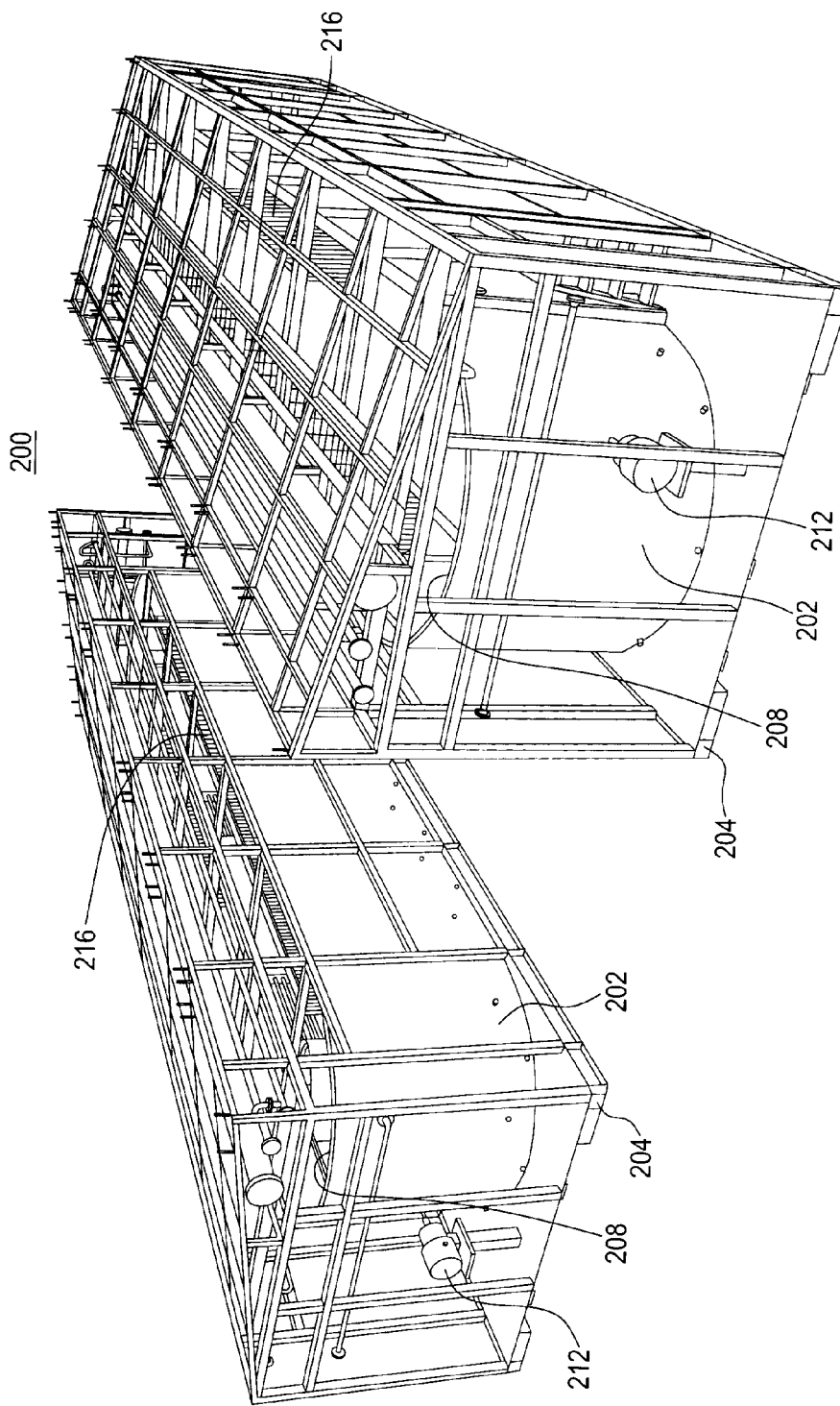
FIG. 9a is a perspective view of an example embodiment of two separated photo-bioreactors within an example embodiment of an enclosure.
Figure 9B:
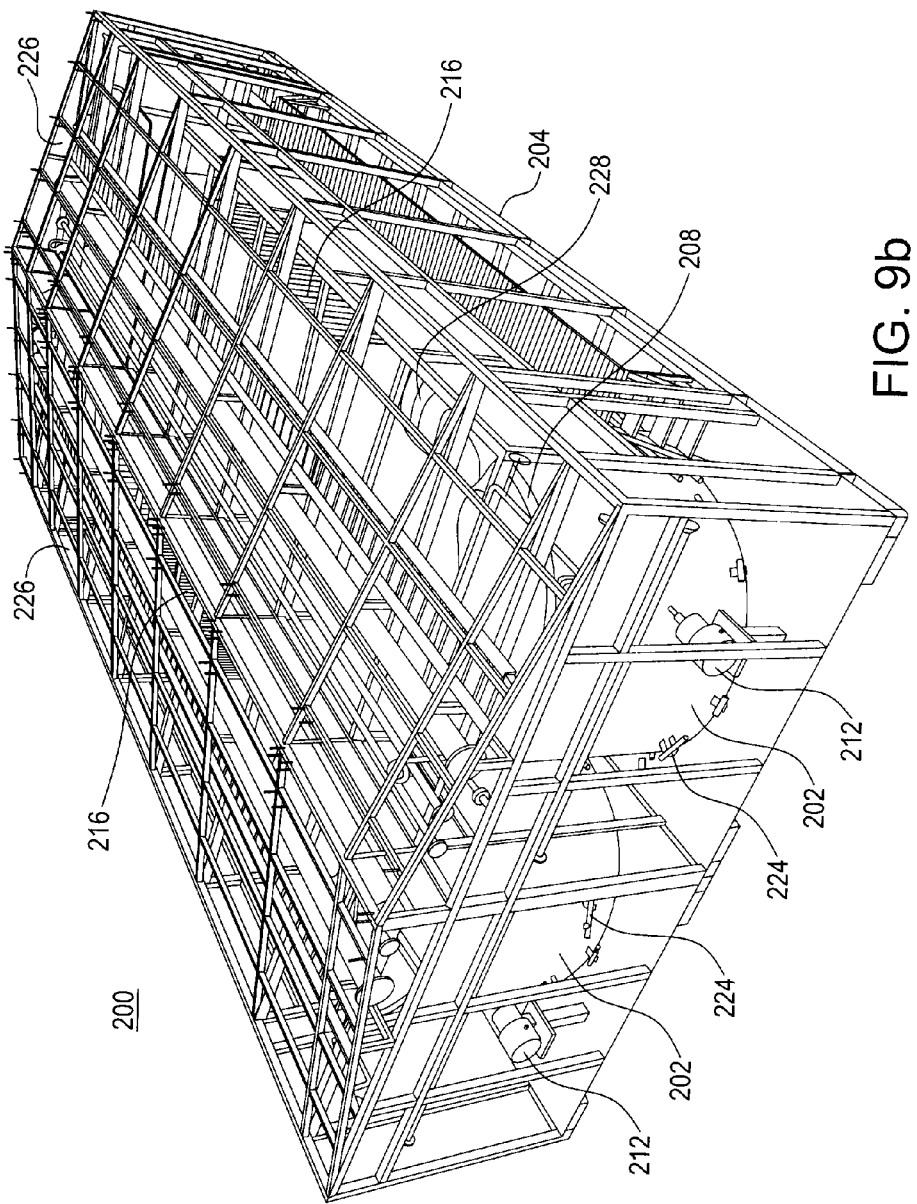
FIG. 9b is a perspective view of an example embodiment of two modularly connected photo-bioreactors within an example embodiment of an enclosure.

The photo-bioreactor 200 can house one or more troughs 202 where algae may be grown. In one aspect the trough can be approximately 48 feet long by 8 feet deep by 10.2 feet wide and generally circular or oval shaped. The trough can be off-set to one side inside of the photo-bioreactor and welded directly to an enclosure structure 204, as shown in FIG. 8. In another embodiment, one enclosure may house a plurality of troughs, as shown in FIG. 9.

Figure 6:
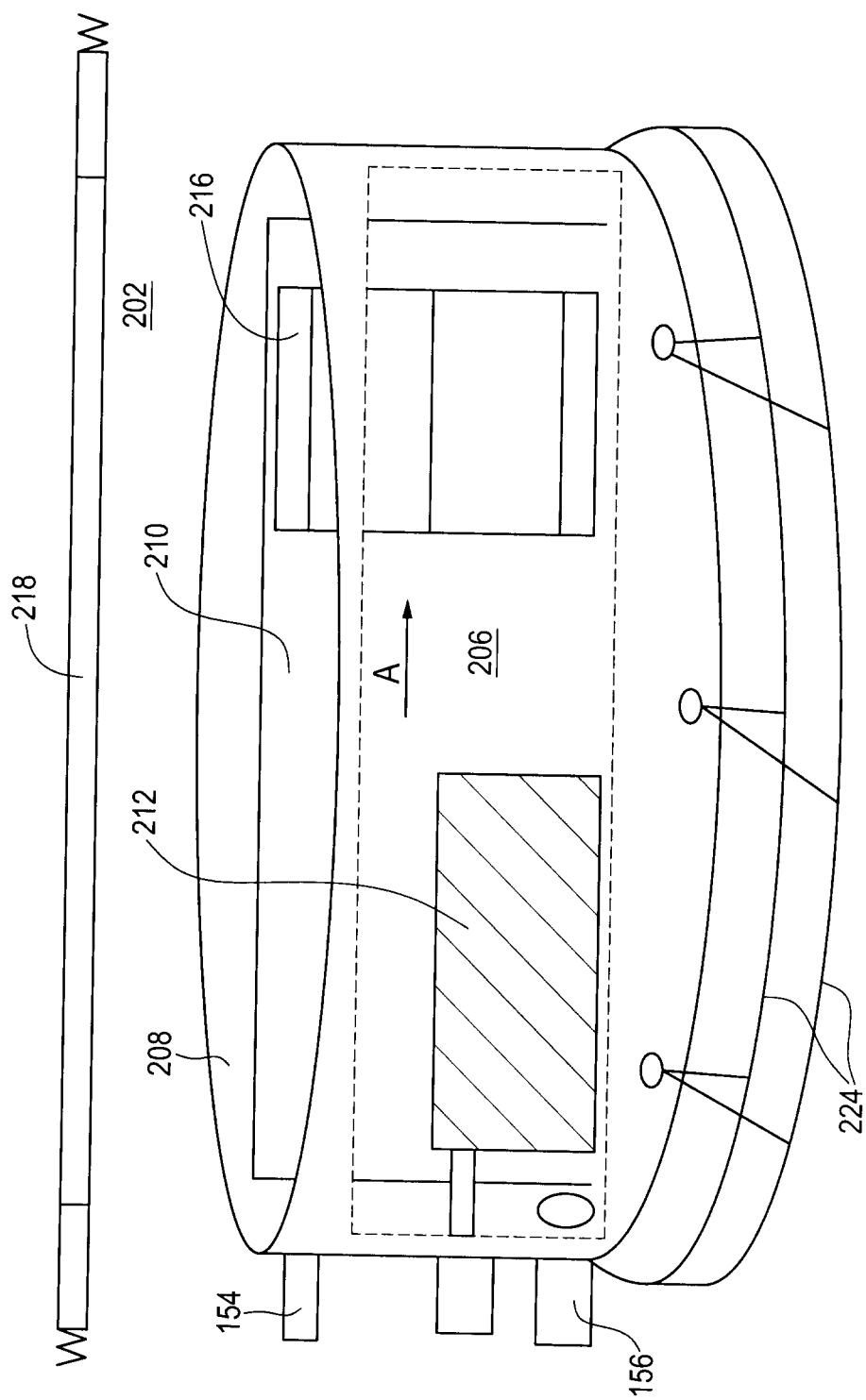
FIG. 6 is a partial cut away, perspective view of an example embodiment of a trough within a photo-bioreactor with the enclosure removed.
Figure 7:
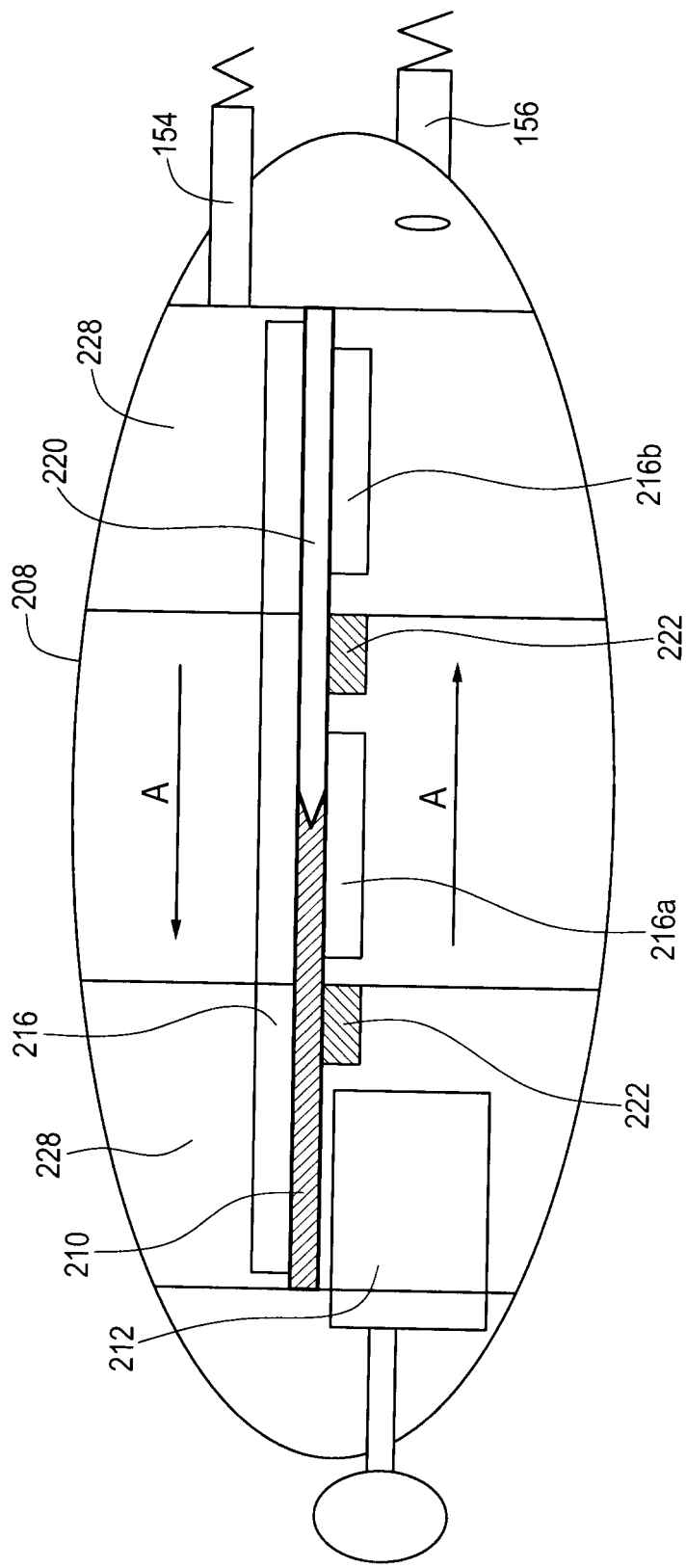
FIG. 7 is a partial cut away, planar, top view of the example embodiment of a photo-bioreactor with the enclosure removed.

FIGS. 6 and 7 depict example embodiments of the trough, for example the trough can define a channel 206 through which water and growth medium can be circulated so that it follows a path through the channel, shown by arrows "A". The inner surface of the trough can be watertight and coated with a durable finish.

In one aspect, the trough may be oval-haped and may be formed of an outer wall 208 and a partition 210 running along the center of the trough from top to bottom. In one aspect, the partition can be positioned so that the width of the channel formed between the outer wall and the partition is substantially equal along its entire oval path, as shown in FIG. 7.

In an alternative embodiment, partition 210 may be positioned so that it is not centered within the trough so that the width of the channel formed between outer wall 208 and partition 210 is unequal along its entire path. For example, partition 210 may be more proximal to one section of the outer wall than another section. As another example, partition 210 may be substantially unparallel to the outer walls. As yet another example, partition 210 may be ripple or wave shaped surface along its height or length dimension.

In any event, the trough may define a circuitous path through which fluid can flow about the partition.

A propulsion unit 212 can be provided in the channel to cause the algae mixture to move through the channel 206. The propulsion unit 212 can be configured so that it creates a current of horizontally flowing algae mixture, through the channel, around the partition, see arrow "A" in FIGS. 6 and 7. For example, propulsion unit 212 may be submerged below the surface of the algae mixture causing flow in one direction, initially away from the propulsion unit, around the partition, then back towards the propulsion unit in a continuous circuit.

In one aspect, the propulsion unit 212 can be a propeller driveshaft mounted through the outer wall of the trough, close to one of the rounded ends of the trough. In another aspect propulsion unit 212 may be an auger or any other suitable propulsion unit. If propulsion unit 212 includes blades, the blades may be fluted to drive the algae mixture and the blades may be sized to turn freely (driven by a motor and planetary gearbox arrangement setup to turn the propeller), with sufficient clearance without contacting the outer wall or the partition while pushing the volume of algae mixture around the channel.

Propulsion unit 212 may also provide vertical agitation or mixing of the algae mixture so that there is significant mixing from the bottom of trough to the surface of algae mixture as the algae mixture circulates around the partition within the channel. Such vertical agitation may, in one embodiment, be generated by canard fins on the blade of propulsion unit 212. Alternatively, the apparatus may include separate units for propelling the algae mixture and agitating it.

In order to facilitate photosynthesis of the algae, and hence its growth, a light source may be provided. Light source may be any natural light and/or artificial light provided by light fixture 216. In one embodiment, which employs light fixture 216, the volume of algae mixture may be circulated through the channel, so that the algae mixture will pass the light source thereby facilitating the photosynthetic consumption of the CO2 from the growth media solution and the production of oxygen, carbohydrates, lipids and other macromolecules as the algae grows.

In one aspect, light fixture 216 can be a single or a plurality of full spectrum LED lighting panels that extend the entire length of, or a portion of, the partition, on one or all sides thereof As another example, light fixture 216 can be a single or a plurality of wide full spectrum LED lighting panels that extend substantially the entire depth of the channel. The panels can be positioned substantially parallel to one another and positioned with their widths substantially parallel to the path of algae mixture circulation through the channel so that algae moving within the current of algae mixture around the trough must flow past the LED-lighted panels. In this manner, the algae mixture circulating through the channel is exposed to light from the light fixture 212 to aid algae growth. Rather than the light reaching only the algae floating proximate surface of the algae mixture in the channel, the light fixture exposes the algae within the entire depth of the channel to light, i.e. from the top of the channel along the entire depth of the channel to the bottom of the channel, and in one aspect the entire length of the partition on one or all sides, allowing a deep channel, through which light only from above the surface level of the algae mixture could not penetrate.

For example, light fixture 216 may be integral to the construction of the floor and the walls of trough 202. Light fixture 216 may be integral to the whole of, or a portion of, the exterior surface of the partition. Further, the light fixture may be a separate component that is separate from the integral structure of trough 202 to facilitate maintenance and, as discussed further below, inter-changeability of light sources to optimize the spectrum of light being provided.

In another aspect, another light fixture 218 may be provided, perhaps in addition to light fixture 216, above the surface of the algae mixture as it circulates through the channel. As described above, the algae mixture may be both circulated and vertically mixed to ensure that substantially all algae is exposed to light fixture 218.

In another aspect, regardless of positioning above or below the surface of the algae mixture, the light fixture may be comprised of a plurality of light fixtures 216a, 216b, 216c, etc. and each individual light source may provide only specific bandwidths of electromagnetic radiation from within an isolated range of the light spectrum. For example, light fixture 216a may provide photonic light energy from the substantially isolated red portion of the spectrum (approximately 610 to 750 nm) whereas light fixture 216b may provide light energy from the substantially isolated range of violet, blue and green portions of the light spectrum (approximately 380 to 570 nm). As one can appreciate, the light fixture may provide full spectrum photonic light energy or the light fixture may provide specific bandwidths of photonic light energy from any portion of the light spectrum. This may provide the advantage allowing the operator to select which bandwidth of light is provided to the algae, for example, a given species or strain of algae may grow optimally in response to a specific bandwidth of light or a species or strain of algae may grow optimally in response to simultaneous exposure to more than one specific bandwidth of light.

In another embodiment, partition 210 can house a heater 220, such as hot-water heater jacket to help control the temperature of water circulating through the channel. Hot water, from boiler 34, or another source can be circulated through one or more chambers inside the partition, exchanging heat with the algae mixture contained in the trough as the liquid solution travels through a water jacket in the partition. In one aspect, smaller, individual heat exchangers 222 may be positioned along, or within, the partition to warm or cool algae mixture to optimize the temperature conditions for the growth of algae.

The photo-bioreactor 200 can be equipped with a separate gas adjustment system 224 plumbed along the base of the outer wall of the trough to adjustably increase CO2 levels in the algae mixture in the trough in order maintain optimal CO2 levels as CO2 is consumed by the algae. Additionally, other gases may be similarly delivered into the base of the trough to provide further vertical agitation of the algae mixture to ensure proper mixing. Other gases may be oxygen or any other suitable gas, or mixture of gases, that is readily available to the apparatus.

As described above, inlet pipe 154 can be provided to route growth media solution from the filter into the trough. Further, an outlet pipe 156 may be provided to route the algae mixture out of trough 202. In one aspect, inlet pipe 154 and outlet pipe 156 can be connected between the trough and enclosure 204 to allow for connection with an external strainer harvesting system 300.

In another embodiment, outlet pipe 156 may be positioned above the base of trough 202 such that gravity draining will only remove a substantially large proportion of the trough's total volume of algae mixture, for example within an approximate range of 40% to 99%, possibly 80%. The remaining or residual volume of algae mixture may be utilized as seed or inoculate in the next cycle of algae growth, for example, approximately 1% to 60%, possibly 20%.

In one aspect, the photo-bioreactors 200 and the water gas mixing unit 100 can be fabricated from steel and/or glass and connected with portable enclosures 204. The photo-bioreactors 200 and the water gas mixing unit 100 can be insulated portable modules allowing them to be moved to a desired location and set up for use.

FIGS. 8 and 9 illustrate example embodiments of modular photo-bioreactors 200. In one aspect, the photo-bioreactor can be enclosed in modular, portable, linkable, insulated enclosure 204. In one aspect, enclosure 204 may be 53 feet long by 12.5 feet high by 14 feet wide, constructed of 8 inch tubular high-strength steel (HSS), welded to form a skid sub base with ¼ inch steel plate flooring. The side and end wall framing may be 6 feet high tubular HSS, spaced 8 feet apart with exterior wall panels 52 consisting of 3/16 inch molded steel sheeting and medium gauge perforated interior wall sheeting with insulation sandwiched between the outer and inner sheeting. The hollow insides of the HSS tubular wall and sub flooring framing can be insulated as well. The upper portion of enclosure 204 can be constructed of 4 inch by 2 inch HSS framing, welded onto the top plate of the 6 feet side and end walls to form an "A" frame which builds up another 2 feet of side and end walls and continues to form the roof framing. The upper portion of the side and end walls and the roof can be insulated green-house type glass panels 226 inserted between the 4×2 inch HSS framing. Enclosures 204 may each have a compressible rubber butt seal and insulated male female coupling housing between each that allows each structure to be pushed tightly together.

In one embodiment, enclosures 204 may be provided with structural support to support the weight of placing one or more other enclosures thereupon. Further, skid sub bases may be re-enforced to provide said structural support, which reinforcement may be achieved by methods known in the art.

Glass panels 226 of enclosure 204 may be transparent or translucent, and therefore may permit the passage of natural light into photo-bioreactor 200 to contribute to the light source and ultimately to assist in the growth of the algae being circulated in the algae mixture around partition 210. Further, due to the aforementioned vertical agitation of the growth media solution, and the algae therein, the issue of surface algae capturing all natural light may be resolved.

In another embodiment, trough 202 may include a covering lid 228 that is connected to either outer wall 208 or partition 210. Covering lid 228 may cover the width of channel 206 substantially along the entire path of the channel. Covering lid 228, for example, may be transparent or translucent to permit the passage of natural light and light from light fixture 216, 218. Covering lid 228 may be a plurality of hingeably connected panels, such as bubble covers, to help capture condensation, provide a physical barrier against contamination, while providing access, for maintenance or otherwise, to the trough, the light fixtures, propulsion unit 212, etc. along the entire path of the channel. So that access may be gained to a section of channel by uncovered one individual covering lid, without disturbing other sections of the channel.

Harvester

Figure 10:
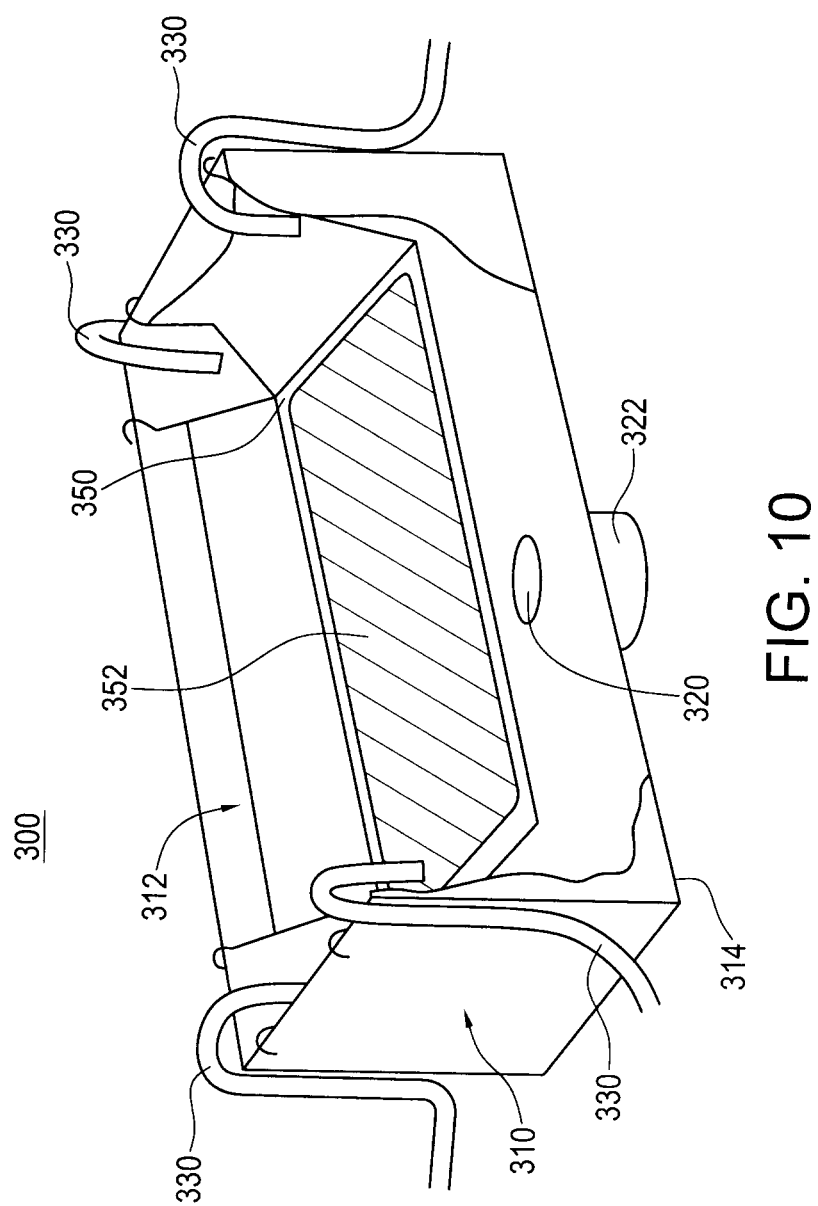
FIG. 10 is a perspective view of an example embodiment of a strainer harvester.

FIG. 10 provides an illustration of an example embodiment of a harvester apparatus 300. Harvester 300 may be connected to one or more photo-bioreactors 200 and which can be used for harvesting the algae grown in these photo-bioreactors. For example, outlet pipe 156 may route growth media solution and algae from one or more troughs to harvester 300.

In one embodiment, the harvester can be fabricated from aluminum, steel or the like and it can be portable, for example, by forklift or on the back of another appropriate vehicle.

In one example embodiment of harvester 300 a strainer harvester system 300 is provided that may have a tank 310. In one aspect, the tank 310 can be fabricated from ¼" ribbed sheets, made of aluminum, steel or the like, with dimension of approximately 12' long by 8' wide by 8' high. The tank 310 may be substantially rectangular with an open top 312, while a bottom 314 of the tank 310 can have four panels constructed to form a slope extending downwards and inwards to a drain hole 320 in the center of the bottom 314 of the tank 310. In this manner, the bottom panel can be funnel-like, designed to direct liquids flowing into the tank to flow into the drain hole in the bottom of the tank. The drain hole can be connected to a pump 322 which in turn can be connected back to the gas mixer unit to recycle any recovered volumes of growth media solution.

A number of inlet pipes 330 can be provided for connecting to outlet pipe 156 from the photo-bioreactor. Each inlet pipe 330 can be routed into the tank 310 to direct algae containing water from the photo-bioreactors into the tank 310. As shown in the example provided in FIG. 10, there may be four inlet pipes 330 conducting algae mixture from four separate troughs.

A strainer basket 350 can be provided in the tank so that water can flow through the strainer basket 350 and exit the drain hole 320 in the bottom of the tank while algae is retained in the strainer basket 350. The strainer basket can be sized to be slightly smaller than the interior of the tank so that it can fit inside the tank. A seat may be provided to hold the strainer basket in place with a gap between the walls of the tank and the strainer basket. In one embodiment, the strainer basket can be fabricated from ¼" perforated aluminum and it may have a substantially flat bottom. It can have 1" pegs welded in place around a rim to hold a wire-mesh impregnated fabric liner 352 in place above the perforations in strainer basket 350 in a manner to allow the growth media solution and the algae therein to flow into the strainer basket 350 and be trapped by liner 352. The water will flow through the liner and the strainer basket down through drain hole 320 to a pump 322 below strainer harvester system 300. The fabric liner will retain the algae and be lifted out once the straining process is complete. The strainer harvester system 300 can be transported by vehicle, such as on the back of a flatbed picker truck. A crane or other lifting device can be used to lift liner 352 from strainer basket 350. The algae may be removed from liner 352 and processed, such as by de-watering, to create an algae derived bio-mass feedstock for various purposes.

The algae-laden water can be circulated through the strainer harvester system as often as required, such as daily. The straining process will separate a significant amount of the algae from the water. A significant portion of the algae can be collected in the strainer basket which contains a removable fabric liner. The liner and its algae content can be lifted from the strainer basket and placed into a dewatering process. The filtered water will gravity flow down through the drain outlet into a high volume pump, which will circulate the strained water back through the head-end unit to start the process again. The dewatered algae will go through an expeller press process to extract the lipids from the algae mass.

In an alternative embodiment of the present invention, there may be a programmable controller system incorporated into one or more elements of the apparatus to automatically regulate the various processes therein. For example, all input streams will flow through a pipe with a remotely controlled valve to provide remote and automated control over the rate at which input streams enter either the pre-dissolving unit 42, the water-gas mixer unit 100. Further, pipe 152 from water-gas mixer unit to move growth media solution to photo-bioreactor 200 may similarly have a remotely and automatically controlled valve to regulate the flow of growth media solution through the purifier unit and the filter unit. Pipes 154 and 156 may similarly have a remotely and automatically controlled valve to regulate the flow of growth media solution from the filter to trough 202 and from the trough to the harvester.

In another aspect, various automated pumps may be employed to automatically and remotely control the flow rates of input streams into the pre-dissolving unit 42, the water-gas mixer unit 100, etc. Further, automated pumps may also control the flow of growth media from water-gas mixer, through purification unit, filter unit to the photo-bioreactor. Similarly, the flow of growth media from the trough to the harvester may also be regulated by automated and remotely controlled pumps.

As described above, an automated control system may be utilized to control the optimization of the growth media within the water-gas mixer unit. The automated control system may be programmable to optimize the conditions of the growth media solution for the species or strain of algae that is going to be grown in a given batch of growth media. The same or a different, automated and programmable control system may be employed to control all the aforementioned remotely and automatically controlled valves, including the propulsion rate of the propulsion unit, the intensity and spectrum of light produced by the light fixtures and the flow of gases in the trough via the gas adjustment system.

Operation

Figure 3:
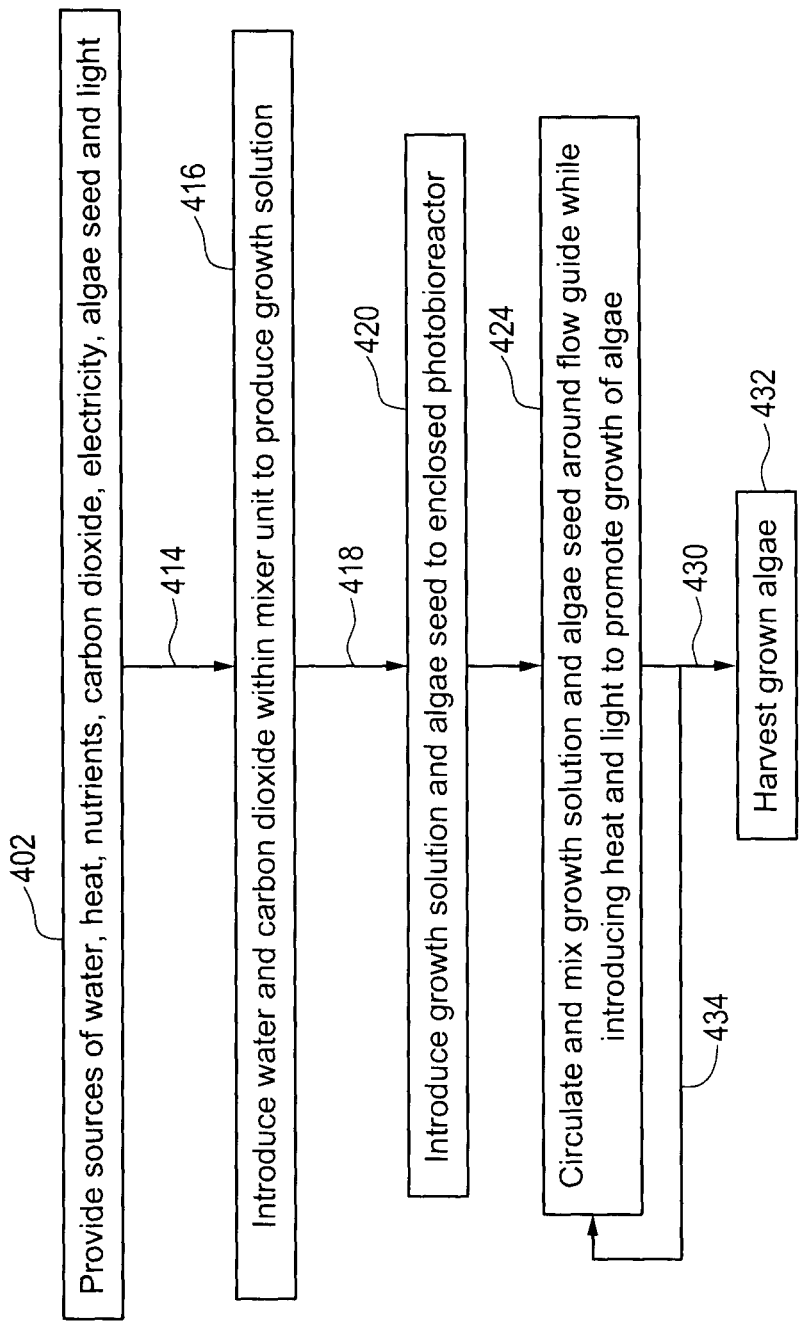
FIG. 3 is a flow diagram of an algae growing and harvesting method in accordance with an example embodiment of the present invention.

In an alternative embodiment of the present invention a method, see FIG. 3, for growing and harvesting algae is disclosed. The method may include the steps of providing input streams of water, heat, nutrients, CO2, electricity, algae seed and light from various sources 402. Of these input streams, water, nutrients and carbon dioxide may be introduced into a mixer unit to produce a growth solution. The growth solution, along with algae seed may be introduced into an enclosed bioreactor with a reactor channel. The growth solution and the algae seed are then mixed within and propelled around the channel while introducing light energy to promote the growth of algae therein. When the algae have grown to a predetermined density, the algae can be removed from the channel and harvested.

A water input stream may be provided from various sources including but not limited to any accessible source of water, including both fresh water and saline water, a municipal water source, a well, an aquifer, and any surface water such as an accessible river, stream, pond, lake or any oceanic body. The advantage of the present invention may be that the water source may further be a wastewater source. For example, wastewater sourced from a wastewater-producing business, nearby municipal water treatment facilities, etc.

CO2 may be provided from any accessible source of carbon dioxide, for example coal fired power plants, cement plants, petroleum refinery plants, fertilizer plants, bio-gas production facilities and any waste streams of CO2 that may be a by-product of many industrial applications.

Similarly a nutrient input stream may be provided from any accessible source of nutrients, for example, liquid fertilizer from an anaerobic digester or a commercially available fertilizer, such as a soluble, granular fertilizer.

An input methane gas input stream may similarly be provided from one or more anaerobic digesters. Methane gas may be used to fuel a gas turbine generator which may similarly be used as a source of CO2, electricity and heat. However, an input electricity stream may also be provided from utility grids, solar panels, wind turbines, geothermal sources and any other electricity streams that may be considered a waste electricity stream.

An input heat stream may be provided from any accessible source of heat, for example a steam boiler 34 that is powered by a gas turbine 32. Heat may also be collected along the various input streams, e.g. waste heat from methane gas, gas turbine generator, flue gases, etc. In an embodiment, the heat may be directed to a heat exchanger to control the temperature of the water source input, and as will be further described below, heat may be directed towards the heat units 40 located throughout the photo-bioreactors 200.

In one aspect, providing an input flue gas stream may be useful as providing a source of carbon dioxide, heat and other nutrients. Such an input flue gas stream may be sourced internally from an algae growth apparatus or externally from cement plants, coal fired power plants, refinery, etc. The input flue gas stream can be continuously pressure-fed to a mixer unit through a pre-dissolving unit, such as a micro bubble pump, high shear static mixer, etc. (not shown) to dissolve the gasses in the water and to distribute the water gas mixture evenly throughout the mixer unit.

Input streams of water and CO2 may be routed to a mixer unit 414. Within the mixer unit, water and carbon dioxide may be introduced and mixed to produce a carbon dioxide rich growth solution 416. The growth solution may then be optimized for conditions such as pH, temperature, CO2 levels and nutrient levels, and purified, filtered and routed to an enclosed photo-bioreactor 418.

The growth medium can then be introduced into an enclosed photo-bioreactor and seeded with a desired strain of algae 420. The seeded growth solution may be mixed and circulated through the photo-bioreactor while exposing the growth solution, the algae seed and algae to light 424. Mixing and circulation of the seeded growth solution may provide that the entire body of seeded growth solution and the algae therein will be exposed to the light at regular frequencies and sufficient durations to aid the growth of the algae. In this manner, the photo-bioreactor 200 can grow algae day or night regardless of natural light conditions.

In an aspect of the present invention, the photo-bioreactor may include a flow guide such that circulation and mixing of the growth solution and the algae therein may flow about the flow guide creating a continuous circuit of growth solution and algae around the flow guide.

In an embodiment of the present invention, the operator may select and optimize the environment within the enclosed photo-bioreactor. For example, the ambient temperature and moisture levels, the temperature, pH, nutrient levels, and carbon dioxide levels of the growth solution may be selected and optimized. The mixing vigor and circulation rate about the flow guide, the intensity, frequency and range of light spectrum within the photo-bioreactor may all be selected to optimize the growth of algae.

When the algae population density has increased to the pre-determined and desired level, the growth solution and the algae may be routed 430 from the photo-bioreactor to a harvest unit for harvesting of the grown algae 432.

As is appreciated in the art, given the optimal conditions algae may undergo 3 to 4 divisions in a day. If algae growth is plotted on a two axis line graph, (indicator of growth on the y-axis and time on the x-axis) a sigmoidal growth curve is typically seen. In that early in the growth phase, under optimal conditions, the slope of the line indicates slower algae growth, sometimes referred to as the lag phase. The middle portion of the curve typically has a much steeper slope indicating a higher rate of algae growth, sometimes referred to as the exponential phase. The middle portion of curve is often followed by a section with a shallower slope than the middle portion, indicating a decrease in the rate of algae growth. This decrease in algae growth rate may be related to the increased competition of algae for the limited resources available within the growth solution and may be referred to as the competition phase. For reasons to be explained herein below, the algae population density level may be pre-determined for routing to the harvester while growth is in or near the end of the exponential phase.

In one embodiment, a residual volume of growth solution and algae may be retained within the photo-bioreactor or routed back to the photo-bioreactor 434. So that when the next batch of fresh growth solution is delivered from the mixer unit, the photo-bioreactor will already be seeded with algae that is already in the exponential phase of growth. With the provision of fresh growth solution and the CO2 and nutrients therein, the exponential growth phase may be perpetuated from one batch to the next. This approach may decrease the time of decreased algae growth associated with both the lag phase and the competition phase. By maintaining the optimal conditions of the next batch of growth solution, within the mixer unit, and within the photo-bioreactor, the exponential growth phase may continue from batch to batch thereby increasing overall outputs of algae biomass from a given photo-bioreactor.

System

Figure 2:
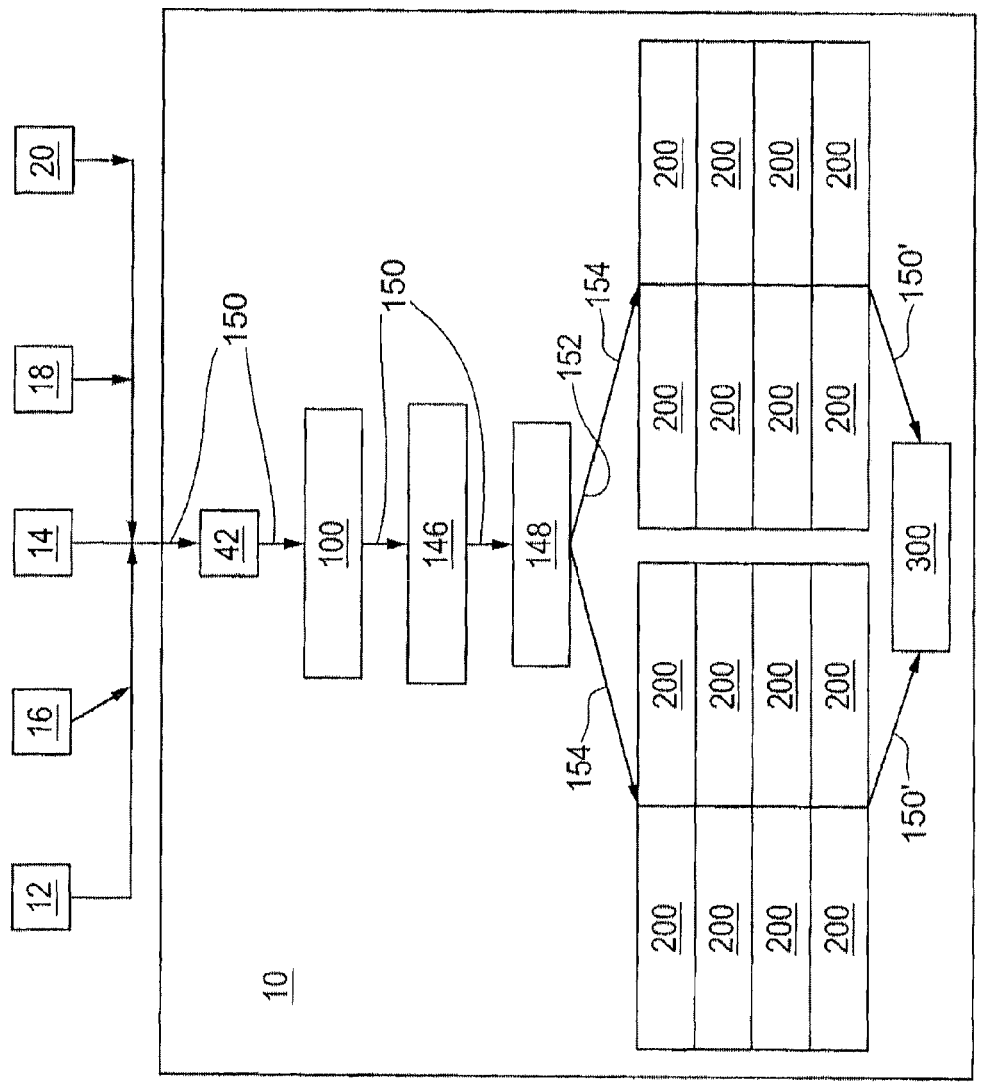
FIG. 2 is a block diagram of an algae growing and harvesting apparatus in accordance with an example embodiment of the present invention.
Figure 4:
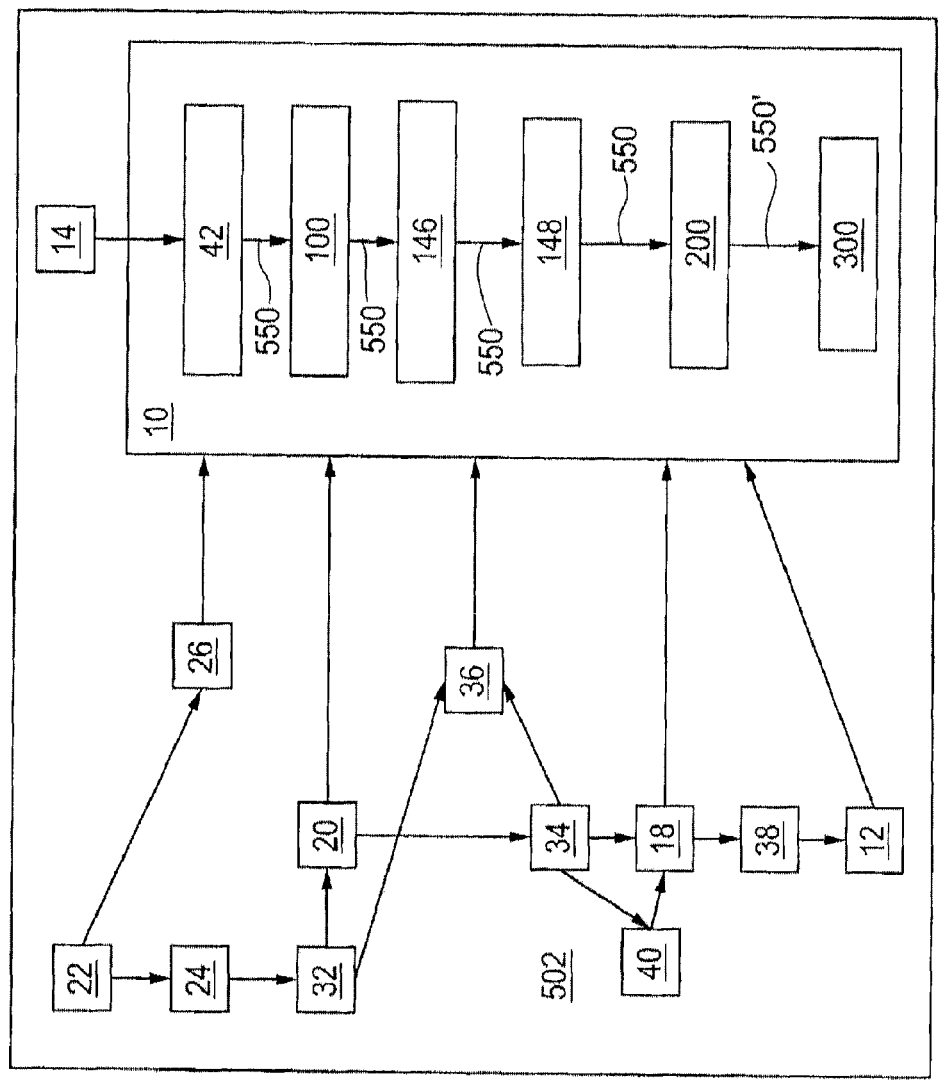
FIG. 4 is a block flow diagram of an algae growing system in one aspect depicting example embodiments of routes for inputs for use with an example algae growth system.

Referring to FIGS. 1, 2 and 4, one can understand how the apparatus described herein above may be subject to an overall control system that may be programmable to automatically control the numerous operational steps of the aforementioned apparatus and methodology.

In one embodiment of the present invention a system 500 is provided for the growth and harvesting of algae, the system comprising: a programmable control (not shown); sources of water 12, carbon dioxide 14, nutrients 16, heat 18, electricity 20, algae seed and light 216; a water-gas mixer 100 to receive and mix the water, heat, carbon dioxide and nutrients, to produce a growth medium stream; a purification unit 146 to receive the source of electricity and the growth medium stream to purify the growth medium; a filtration unit to receive and filter the purified growth medium 150, 550; at least one enclosed reactor trough to receive and propel the growth medium around a partition while introducing the algae seed source to the growth medium to seed and further introducing the light source to the seeded growth medium to cultivate algae growth; a harvesting unit to receive the algae growth 150', 550'; and the programmable control assembly controlling the water-gas mixer's receipt of the water, nutrients, carbon dioxide, and electricity the programmable control assembly controlling the purification and filtering of the growth medium stream, the assembly controlling the receipt and propulsion of the purified and filtered growth media stream, the introduction of light and algae seed and the receipt of the algae growth by the harvesting unit.

In an embodiment of the present invention, the system may include multiple enclosed reactor troughs within a given enclosure, for example two troughs may be within the same enclosure. Further, multiple enclosures may be linked with a given water-gas mixer, purifier and filter. For example, a single water-gas mixer may be upstream from one purifier and one filter, however, there may be upwards of 16 enclosures, or 32 troughs per water-gas mixer. It is granted that more than 16 enclosures may be downstream from a given water-gas mixer; however economic factors may influence the incentive for such expansion.

A particular advantage of the system may be the isolated feature of each trough. In that the only common stream into each trough is the purified and filtered growth medium. As described above, the seeding of algae only occurs within the trough itself. This allows for a diversity of algae biomass production within a given system because multiple troughs all receiving a purified and filtered growth medium stream can support any number of different species and strains of algae within a given system. For example, one species may be grown within one trough and a different species may be grown within one enclosure and a different species may be grown in a separate enclosure. Further, two species of algae may be grown within two troughs, each within the same enclosure.

An additional advantage of the isolated nature of each trough is the ability to address contamination on a "per trough" or "per enclosure" basis. For example, should it be determined that one trough becomes contaminated with an algae species that is different from, or even competitive with or predatory to, the target species the trough may be emptied of both species, cleaned, de-contaminated and then refilled with purified and filtered growth medium and then seeded with the target species.

In an alternative embodiment, the system may provide for a culture maintenance program whereby specific maintenance troughs may be constantly maintained with a population of the target algae species. Such that in the event of a contamination, emptying, cleaning and decontamination of a trough, that trough may readily be re-seeded with the target species from the maintenance trough and decreasing the time for turn around.

In another embodiment, the system may include a gas turbine generator 32 and an extraction plant facility (not shown). Bio-gas, such as methane gas, from the anaerobic digester 22 can be used to help drive the gas turbine generator 30. Some of the residual algae organic waste or another source of bio-mass can be routed into the anaerobic digester 22 to produce methane gas and a fertilizer. The methane gas produced may be combusted in the gas turbine generator 30 to produce electricity. The gas turbine generator 30 can be used to supply electrical power to all elements of the system that require such power, for example the programmable control 502, purification unit 146, the filter 148, pumps 122, propulsion unit 212, light fixtures 216, harvesting units 300, extraction and processing plant operations (not shown) and the various remotely controlled valves and pumps of the system 500. The gas turbine generator 30 and boiler 32 will emit exhaust flue gases which may be fed into the water gas mixing unit 100.

Further, based upon the insulation and portability of the all elements of the system, the system may be installed at any location, regardless of geographical climatic conditions, with a lower requirement for land in comparison to the known open algae growth systems.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

What is claimed is:

1. An apparatus for the growth and harvesting of algae, the apparatus comprising:

(a) a trough for housing an algae mixture, the trough including an inlet and an outlet, a partition within the trough, a heater in the partition to apply heat to the algae mixture, a light source positioned within the trough, the light source including a submersible LED light fixture, a propulsion member for circulating the algae mixture within the trough around the partition and past the light source and a transparent lid over the trough for condensation control, the lid including a plurality of hingeably connected bubble covers covering the trough;

(b) a water-gas mixer for producing growth media, the water-gas mixer located upstream from the trough, the water-gas mixer including an inlet and an outlet, the outlet being in fluid communication with a conduit through which the growth media is introduced through the inlet of the trough;

(c) a harvester to receive the algae mixture from the outlet of the trough, the harvester configured for separating algae from the growth media; and (d) a support base for supporting the trough and an enclosure installed on the support base and enclosing about at least the trough, the enclosure including insulated side panels and a roof including glass panels to permit natural light to access the trough from outside the enclosure.

2. The apparatus of claim 1, the heater being a heat exchanger.

3. The apparatus of claim 1, wherein the light source provides one range of light from the light spectrum.

4. The apparatus of claim 1, wherein the submersible LED fixture emits full spectrum light.

5. The apparatus of claim 1, wherein the water-gas mixer is insulated.

6. The apparatus of claim 1, wherein the outlet from the trough is configured to allow a large portion of the algae mixture to the harvester.

7. The apparatus of claim 1, wherein the enclosure support base and the glass panels are insulated.

8. The apparatus of claim 1, the propulsion member further comprising a vertical agitator to provide vertical agitation of the algae mixture.

9. The apparatus of claim 1, further comprising a programmable control system for controlling the flow rate of input streams, the routing rate of growth media to the trough and the flow of the algae mixture to the harvester.

10. The apparatus of claim 1, wherein the support base is a skid to thereby render the enclosure and the trough modular and portable and the enclosure is connectible to another enclosure.

11. The apparatus of claim 10, wherein the glass panels are insulated glass panels.

* * * * *